United States Patent [19]

Crimmin et al.

[11] Patent Number: 5,691,382
[45] Date of Patent: Nov. 25, 1997

[54] INHIBITION OF TNF PRODUCTION WITH MATRIX METALOPROTEINASE INHIBITORS

[75] Inventors: Michael John Crimmin; William Alan Galloway; Andrew John Hubert Gearing, all of Cowley, Great Britain

[73] Assignee: British Biotech Pharmaceuticals Limited, Oxford, England

[21] Appl. No.: 436,190

[22] PCT Filed: Nov. 12, 1993

[86] PCT No.: PCT/GB93/02331

§ 371 Date: May 12, 1995

§ 102(e) Date: May 12, 1995

[87] PCT Pub. No.: WO94/10990

PCT Pub. Date: May 26, 1994

[30] Foreign Application Priority Data

Nov. 13, 1992 [GB] United Kingdom ............... 9223904

[51] Int. Cl.$^6$ .................................................. A61K 31/19
[52] U.S. Cl. ........................................................... 514/575
[58] Field of Search ............................................... 514/575

[56] References Cited

U.S. PATENT DOCUMENTS 4,599,361  7/1986  Fukami et al. ...................... 514/575

FOREIGN PATENT DOCUMENTS

| 0236872 | 9/1987 | European Pat. Off. . |
| 0274453 | 7/1988 | European Pat. Off. . |
| 0489577 | 6/1992 | European Pat. Off. . |
| 9005716 | 5/1990 | WIPO . |
| 9005719 | 5/1990 | WIPO . |
| 9102716 | 3/1991 | WIPO . |

*Primary Examiner*—William R. A. Jarvis
*Attorney, Agent, or Firm*—Hale and Dorr LLP

[57] ABSTRACT

The present invention is directed to the method of inhibiting the release of tumor necrosis factor (TNF) in a condition mediated by TNF by administration of certain hydroxamic add derivatives, also known as matrix metalloproteinase inhibitors, and thus the method of this invention is useful in the management of diseases or conditions mediated by TNF.

18 Claims, No Drawings

INHIBITION OF TNF PRODUCTION WITH MATRIX METALOPROTEINASE INHIBITORS

This application claims priority to PCT/GB93/02331 filed Nov. 12, 1993, published as WO94/10990 May 26, 1994, published as WO94/10990 May 26, 1994.

This invention relates to a new pharmaceutical and veterinary use of certain hydroxamic acid derivatives, previously known in the art as inhibitors of matrix metalloproteinases such as collagenase. In accordance with the invention the known compounds have been found to be capable of inhibiting the production of tumour necrosis factor (TNF) by cells, and thus to be useful in the management of diseases or conditions mediated by overproduction of, or over-responsiveness to, TNF.

BACKGROUND OF THE INVENTION

TNF

TNF is a cytokine which is produced initially as a cell-associated 28 kD precursor. It is released as an active, 17 kD form (Jue, D-M et al., (1990) Biochemistry 29:8371–8377), which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Preventing the production or action of TNF is, therefore, predicted to be a potent therapeutic strategy for many inflammatory, infectious, immunological or malignant diseases.

It has been shown that the effects of TNF are mediated by two peptides, TNF α and TNF β. Although these peptides have only 30% homology with each other, they activate the same receptors and are encoded by immediately adjacent genes. As used herein, the term tumour necrosis factor or TNF therefore means tumour necrosis factor α and peptides having a high degree of sequence homology with, and substantially similar physiological effects to, TNF α, for example TNF β.

MMP Inhibitors

It is known that metalloproteinases such as collagenase, stromelysin and gelatinase (known as "matrix metalloproteinases", and herein referred to as MMPs) are involved in connective tissue breakdown. The known hydroxamic acid-based MMP inhibitors with which this invention is concerned are those forming part of the state of the art by virtue of any of the following patent publications:

| | |
|---|---|
| US 4599361 | ("Searle") |
| EP-A-0236872 | ("Roche 1") |
| EP-A-0274453 | ("Bellon") |
| WO 90/05716 | (British Biotechnology) ("BBL1") |
| WO 90/05719 | (British Biotechnology) ("BBL2") |
| WO 91/02716 | (British Biotechnology) ("BBL3") |
| EP-A-0489577 | ("Celltech 1") |

-continued

| | |
|---|---|
| EP-A-0489579 | ("Celltech 2") |
| EP-A-0497192 | ("Roche 2") |
| WO 92/13831 | (British Biotechnology) ("BBL4") |
| WO 92/22523 | (Research Corporation Technologies) ("RCT") |
| WO 93/09090 | ("Yamanouchi") |
| WO 93/09097 | ("Sankyo") |

The disclosure of each of those publications is hereby incorporated by reference, and the reader is referred thereto for details of the structures of the compounds disclosed and methods for their preparation. The MMP inhibiting hydroxamic acid derivatives disclosed therein can be regarded as having the following basic structure (I):

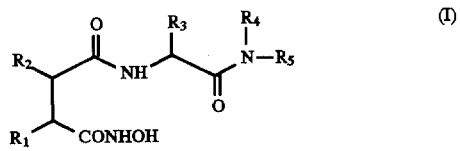

wherein the five substituents $R_1$–$R_5$ may vary according to the detailed disclosure of each publication. However, neither the compounds per se nor the method of their preparation form part of this invention. Rather, the invention arises from the finding by the present inventors that representative members of the compound classes disclosed in each of those publications have the property of inhibiting release of TNF from cells, and the realisation that such activity is widespread amongst the disclosed compounds.

General Composite Structural Definition of Known MMP Inhibitors

Without prejudice to the true disclosures of the patent publications listed above, the following general composite structural definition of the disclosed compounds is offered as a guide. It has been compiled from the structural disclosures of the publications, but where further information is required concerning the identity of the compounds with which the present invention is concerned, the reader must consult the publication in question. Furthermore, where conflict arises between the disclosure of any of the patent publications listed above and the general composite structural definition set out below, the former prevails:

The aforesaid composite structural definition is of compounds of formula (I) or (Ib)

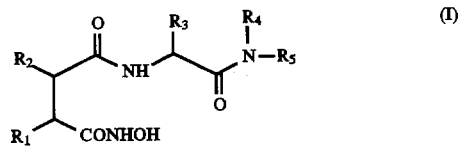

wherein the five substituents $R_1$–$R_5$ may vary as follows:

$R_1$ (Searle) hydrogen, $C_1$–$C_6$ alkyl, phenyl, phenyl($C_1$–$C_6$ alkyl); (Roche 1) hydrogen, $NH_2$, OH, SH, $C_1$–$C_6$ alkyl, $C_1$–$C_6$ alkoxy, $C_1$–$C_6$ alkylamino, $C_1$–$C_6$ alkylthio or aryl($C_1$–$C_6$ alkyl) group or amino-$C_1$–$C_6$ alkyl, hydroxy-$C_1$–$C_6$ alkyl, mercapto-$C_1$–$C_6$ alkyl or carboxy-$C_1$–$C_6$ alkyl where the amino-, hydroxy-, mercapto or carboxyl group can be protected, the amino group acylated or the carboxyl group amidated;

(Bellon) hydrogen;

(BBL1) hydrogen, $C_1$–$C_6$ alkyl, $C_2$–$C_6$ alkenyl, phenyl, phenyl($C_1$–$C_6$ alkyl), or a group $BSO_nCH_2$— wherein n is 0, 1 or 2 and B is hydrogen or a ($C_1$–$C_6$) alkyl, phenyl, substituted phenyl, phenyl($C_1$–$C_6$)alkyl, or heterocyclyl group;

(BBL2) a group BSO$_n$A— wherein n is 0, 1 or 2 and B is hydrogen or an alkyl, phenyl, substituted phenyl, phenylalkyl, heterocyclyl, alkylcarbonyl, phenacyl or substituted phenacyl group, and A represents a hydrocarbon chain optionally substituted with one or more alkyl, phenyl, or substituted phenyl groups;

(BBL3) hydrogen or a (C$_1$–C$_6$)alkyl, (C$_2$–C$_6$)alkenyl, phenyl, phenyl(C$_1$–C$_6$)alkyl, (C$_1$–C$_6$)alkylthiomethyl, phenylthiomethyl, substituted phenylthiomethyl, phenyl(C$_1$–C$_6$)alkylthiomethyl or heterocyclylthiomethyl group;

(Celltech 1) optionally substituted alkyl, alkenyl, aryl, aralkyl, heteroaralkyl, or heteroarylthioalkyl;

(Celltech 2) optionally substituted alkyl, alkenyl, aryl, aralkyl, heteroaralkyl, or heteroarylthioalkyl;

(Roche 2) hydrogen, amino, protected amino, acylamino, or lower alkyl optionally substituted by aryl, hydroxy, protected hydroxy, amino, protected amino, acylamino, maleimido, succinimido, naphthalimido, 2,3-dihydro-1,3-dioxo-1H-benz[d,e]isoquinol-2-yl, carboxy, protected carboxy, carbamoyl, mono(lower alkyl) carbamoyl, di(lower alkyl)carbamoyl, di(lower alkyl) amino, carboxy-lower alkanoylamino, pyrrolidino or morpholino;

(BBL4) hydrogen (C$_1$–C$_6$)alkyl, phenyl, substituted phenyl, phenyl(C$_1$–C$_6$)alkyl, or heterocyclyl; or R$^1$ represents ASO$_n$R$^7$ wherein A represents a (C$_1$–C$_6$) hydrocarbon chain, optionally substituted with one or more (C$_1$–C$_6$)alkyl, phenyl or or substituted phenyl groups and n=0, 1 or 2; R$^7$ is (C$_1$–C$_6$)alkyl, phenyl, substituted phenyl, phenyl (C$_1$–C$_6$) alkyl, heterocyclyl, (C$_1$–C$_6$)alkyl, (C$_1$–C$_6$)acyl, thienyl or phenacyl;

("RCT") hydrogen, lower alkyl, aryl, or aryl lower alkyl;

(Yamanouchi) lower alkyl which may be substituted by a substituent selected from mercapto, loweralkylthio, arylthio and lower acylthio;

(Sankyo) hydrogen;

R$_2$ (Searle) hydrogen, phenyl, phenyl(C$_1$–C$_6$ alkyl), cycloalkyl, cycloalkyl(C$_1$–C$_6$ alkyl);

(Roche 1) C$_2$–C$_5$ alkyl;

(Bellon) isobutyl;

(BBL 1) hydrogen atom or an (C$_1$–C$_6$)alkyl, (C$_2$–C$_6$) alkenyl, phenyl(C$_1$–C$_6$)alkyl, cycloalkyl (C$_1$–C$_6$)alkyl or cycloalkenyl (C$_1$–C$_6$)alkyl group;

(BBL2) a hydrogen atom or an alkyl, alkenyl, phenylalkyl, cycloalkylalkyl or cycloalkenylalkyl group;

(BBL3) a hydrogen atom or an (C$_1$–C$_6$)alkyl, (C$_2$–C$_6$) alkenyl, phenyl(C$_1$–C$_6$)alkyl, cycloalkyl (C$_1$–C$_6$)alkyl or cycloalkenyl (C$_1$–C$_6$)alkyl group;

(Celltech 1) optionally substituted alkyl, alkenyl, cycloalkyl, aryl, aralkyl, aralkoxy, or aralkylthio group, or an amino, substituted amino, carboxyl, or esterified carboxyl group;

(Celltech 2) optionally substituted phenylethyl, phenylpropyl or phenylbutyl group;

(Roche 2) isobutyl;

(BBL4) hydrogen or an (C$_1$–C$_6$)alkyl, (C$_2$–C$_6$)alkenyl, phenyl(C$_1$–C$_6$)alkyl, or cycloalkyl (C$_1$–C$_6$)alkyl group;

("RCT") hydrogen, lower alkyl, aryl, or aryl lower alkyl;

(Yamanouchi) a group —Y—X—Z wherein Y is a single bond or lower alkylene, X is O or S, and Z is lower alkyl;

(Sankyo) hydrogen, alkyl or aralkyl;

(Searle) C$_1$–C$_6$ alkyl, benzyl, benzyloxybenzyl, (C$_1$–C$_6$ alkoxy)benzyl, benzyloxy(C$_1$–C$_6$ alkyl);

(Roche 1) the characterising group of a natural α amino acid, which may be protected if functional groups are present, eg acylation of amino groups and amidation of carboxylgroups, with the provision that R$_3$ is not H or methyl;

(Bellon) isopropyl, 4-aminobutyl, n-butyl, 2-methylmercaptoethyl;

(BBL1) an amino acid residue with R or S stereochemistry or a (C$_1$–C$_6$)alkyl, benzyl, (C$_1$–C$_6$)alkoxy benzyl or benzyloxy (C$_1$–C$_6$)alkyl group;

(BBL2) an amino acid residue with R or S stereochemistry or a (C$_1$–C$_6$)alkyl, benzyl, (C$_1$–C$_6$ alkoxy) benzyl or benzyloxy (C$_1$–C$_6$ alkyl) group;

(BBL3) an amino acid residue with R or S stereochemistry or a (C$_1$–C$_6$)alkyl, benzyl, (C$_1$–C$_6$)alkoxy benzyl, benzyloxy (C$_1$–C$_6$)alkyl or benzyloxybenzyl group;

(Celltech 1) a group -[Alk]$_n$R$^6$ where Alk is an alkyl or alkenyl group optionally interrupted by one or more —O—, or —S— atoms or —N(R$^7$)-groups [where R$^7$ is a hydrogen atom or a C$_1$–C$_6$ alkyl group], n is zero or an integer 1, and R$^6$ is an optionally substituted cycloalkyl or cycloalkenyl group;

(Celltech 2) optionally substituted alkyl or alkenyl group optionally interrupted by one or more —O—, or —S— atoms or —N(R$^7$)-groups [where R$^7$ is a hydrogen atom or a C$_1$–C$_6$ alkyl group];

(Roche 2) tert-butyl;

(BBL4) a benzyl group with one or two substituents in the phenyl ring selected from hydrogen, halogen, cyano amino, amino (C$_1$–C$_6$)alkyl, amino di (C$_1$–C$_6$)alkyl, amino (C$_1$–C$_6$)alkylacyl, aminophenacyl, amino (substituted)phenacyl, amino acid or derivative thereof, hydroxy, oxy (C$_1$–C$_6$)alkyl, oxyacyl, formyl, carboxylic acid, carboxamide, carboxy (C$_1$–C$_6$)alkylamide, carboxyphenylamide, carboxy (C$_1$–C$_6$)alkyl, hydroxy (C$_1$–C$_6$)alkyl, (C$_1$–C$_6$)alkyloxy (C$_1$–C$_6$)alkyl or acyloxy (C$_1$–C$_6$)alkyl, (C$_1$–C$_6$)alkylcarboxylic acid, or (C$_1$–C$_6$)alkylcarboxy (C$_1$–C$_6$)alkyl, amino(C$_1$–C$_6$) alkylacyl carboxylic acid or amino(C$_1$–C$_6$) alkylcarboxylate; or a benzyl group with one substituent in the phenyl ring selected from groups of formula —OCH$_2$CN, —OCH$_2$COR$^8$ and —OCH$_2$CH$_2$OR$^9$, where R$^8$ is hydroxyl, (C$_1$–C$_6$)oxyalkyl, (C$_1$–C$_6$) oxyalkylphenyl, amino, (C$_1$–C$_6$)aminoalkyl, (C$_1$–C$_6$) aminodialkyl, (C$_1$–C$_6$)aminoalkylphenyl, an amino acid or derivative thereof; and R$^9$ is (C$_1$–C$_6$)alkyl, (C$_1$–C$_6$)alkylphenyl, phenyl, substituted phenyl (C$_1$–C$_6$)alkylacyl or phenacyl;

("RCT") aryl lower alkyl, or heterocyclic lower alkyl, either being unsubstituted or mono- or di-substituted with fluoro, bromo, chloro, halo, nitro, carboxy, lower carbalkoxy, cyano, lower alkanoyl, trifluoromethyl lowere alkyl, hydroxy, lower alkoxy, formyl, amino, lower alkyl amino, di-lower alkyl amino, mercapto, lower alkylthio, or mercapto lower alkyl;

(Yamanouchi) 4-(lower alkyl)phenylmethyl;

(Sankyo) a group —CH$_2$—CH$_2$—CH$_2$—NH— where the right hand bond is formed with the N atom adjacent the C atom carrying R$_3$, thereby replacing the H atom shown on that C atom in formula (I);

R$_4$ (Searle) C$_1$–C$_6$ alkyl;

(Roche 1) a group —CHBD wherein B is H or methyl and D is H or C$_1$–C$_6$ alkyl, C$_1$–C$_6$ alkoxy-C$_1$–C$_6$ alkyl, di($C_1$–$C_6$ alkoxy)methyl, carboxy, $C_1$–$C_6$ alkylcarbonyl, $C_1$–$C_6$ alkoxycarbonyl, arylmethoxycarbonyl, $C_1$–$C_6$ alkylaminocarbonyl or arylaminocarbonyl, or B and D together form a trimethylene group; or $R_3$ and B together form a group $(CH_2)n$ where n is an integer from 4–11 ;

(Bellon) hydrogen, phenyl($C_1$–$C_2$ alkyl), or trifluoromethylphenyl($C_1$–$C_2$ alkyl);

(BBL1) a group —$(CH_2)_n$A wherein n is an integer from 1 to 6 and A represents the group —$NH_2$, a substituted acyclic amine or a heterocyclic base;

(BBL2) a hydrogen atom or a ($C_1$–$C_6$)alkyl group;

(BBL3) a group $(CH_2)_n$A wherein n is an integer from 1 to 6 and A represents a hydroxy, ($C_1$–$C_6$)alkoxy, ($C_2$–$C_7$)acyloxy, ($C_1$–$C_6$)alkylthio, phenylthio, ($C_2$–$C_7$)acylamino or N-pyrrolidone group;

(Celltech 1) a hydrogen atom, an optionally substituted straight or branched alkyl group, optionally interrupted by one or more —O— or —S— atoms or —N($R^7$)- groups [where $R^7$ is a hydrogen atom or a $C_1$–$C_6$ alkyl group], or aminocarbonyloxy groups; or $R^4$ and $R^5$ together with the nitrogen atom to which they are attached may form an optionally substituted $C_3$–$C_6$ cyclic amino group optionally possessing one or more other heteroatoms selected from —O— or —S— or —N($R^7$)-groups [where $R^7$ is a hydrogen atom or a $C_1$–$C_6$ alkyl group];

(Celltech 2) a hydrogen atom, an optionally substituted straight or branched alkyl group, optionally interrupted by one or more —O— or —S— atoms or —N($R^7$)- groups [where $R^7$ is a hydrogen atom or a $C_1$–$C_6$ alkyl group], or aminocarbonyloxy groups; or $R^4$ and $R^5$ together with the nitrogen atom to which they are attached may form an optionally substituted $C_3$–$C_6$ cyclic amino group optionally possessing one or more other heteroatoms selected from —O— or —S— or —N($R^7$)-groups [where $R^7$ is a hydrogen atom or a $C_1$–$C_6$ alkyl group];

(Roche 2) hydrogen or lower alkyl optionally substituted by aryl, amino, protected amino, di(lower alkyl)amino, guanidino, carboxyl, protected carboxyl, carbamoyl, mono(lower alkyl)carbamoyl, di(lower alkyl) carbamoyl, di(lower alkyl)phosphinyl, dihydroxyphosphinyl, pyrrolidino, piperidino or morpholino;

(BBL4) hydrogen or a ($C_1$–$C_6$)alkyl, or phenyl($C_1$–$C_6$) alkyl group;

("RCT") a group —XD wherein X is a bond, lower alkylene, or a group —$(CAB)_m$—C(O)—N(Z)—, or —$(CAB)_m$—$CH_2$O—, or —$(CAB)_m$—C(O)O— wherein A is hydrogen, methyl or ethyl, and B and Z are independently hydrogen or lower alkyl, and m is 1,2 or 3 with the proviso that when X is a chemical bond then the group $R_3$ (see above for RCT definition of $R_3$) is not unsubstituted benzyl or benzyl monosubstituted with hydroxy or lower alkoxy, and the further proviso that when X is a group —$(CAB)_m$—C(O)—N(Z)— wherein m is 1 and A, B and Z are as defined above, then the group $R_3$ (see above for RCT definition of $R_3$) is not indole or imidazole or unsubstituted benzyl or benzyl substituted with hydroxy or lower alkoxy;

(Yamanouchi) lower alkyl;

(Sankyo) hydrogen, alkyl, alkoxy, or (when $R^5$ is hydrogen) —CH($R^6$)$COR^7$ where $R^6$ is hydrogen or alkyl and $R^7$ is alkyl, or —CH($R^6$)$COOR^8$ where $R^6$ is hydrogen or alkyl and $R^8$ is alkyl, or —CH($R^6$)$CONR^9R^{10}$ where $R^9$ and $R^{10}$ are each alkyl, or $R^4$ taken together with $R^5$ and the nitrogen atom to which they are attached form a heterocyclic group;

$R_5$ (Searle) hydrogen;

(Roche 1) H or methyl;

(Bellon) hydrogen;

(BBL1) a hydrogen atom or a methyl group;

(BBL2) a hydrogen atom or a methyl group;

(BBL3) a hydrogen atom or a methyl group;

(Celltech 1 ) a hydrogen atom, an optionally substituted straight or branched alkyl group, optionally interrupted by one or more —O— or —S— atoms or —N($R^7$)- groups [where $R^7$ is a hydrogen atom or a $C_1$–$C_6$ alkyl group], or aminocarbonyloxy groups;

(Celltech 2) a hydrogen atom, an optionally substituted straight or branched alkyl group, optionally interrupted by one or more —O— or —S— atoms or —N($R^7$)- groups [where $R^7$ is a hydrogen atom or a $C_1$–$C_6$ alkyl group], or aminocarbonyloxy groups;

(Roche 2) hydrogen;

(BBL4) hydrogen or methyl;

("RCT") hydrogen or lower alkyl;

(Yamanouch) hydrogen;

(Sankyo) hydrogen or alkyl.

In addition, the publication (Roche 1 ) discloses "reverse hydroxamic acid" MMP inhibitors of formula (Ib)

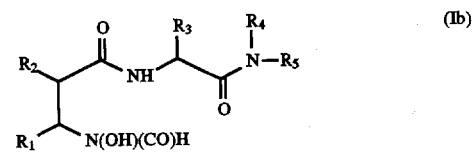

(Ib)

wherein the substituents $R_1$–$R_2$ are the "Roche 2 substituents defined above in relation to formula (I). Salts of such known MMP inhibitors include physiologically acceptable acid addition salts for example hydrochlorides, hydrobromides, sulphates, methane sulphonates, p-toluenesulphonates, phosphates, acetates, citrates, succinates, lactates, tartrates, fumerates and maleates. Salts may also be formed with bases, for example sodium, potassium, magnesium, and calcium salts.

There are several chiral centres in such known MMP inhibitors because of the presence of asymmetric carbon atoms. The presence of several asymmetric carbon atoms gives rise to a number of diastereomers with R or S Stereochemistry at each chiral centre. General formula (I), and (unless specified otherwise) all other formulae in this specification are to be understood to include all such stereoisomers and mixtures (for example racemic mixtures) thereof.

The preferred stereochemistry is in general as follows:

C atom adjacent the —CONHOH moiety —S,

C atom adjacent the $R_2$ group —R,

C atom adjacent the $R_3$ group —S, but mixtures in which the above configurations predominate are also contemplated.

Reduced Composite Structural Definition of Known MMP Inhibitors

Again without prejudice to the true disclosures of the patent publications listed above, the following reduced composite definition of the disclosed compounds is offered, it being understood that where further information is required concerning the identity of the disclosed compounds, the reader must consult the publication in question. The reduced composite definition is restricted to a core sub-set of the totality of structures encompassed by the patent publications listed above, namely compounds of formula (I) or (Ib):

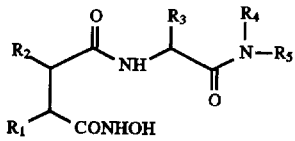

wherein the five substituents $R_1-R_5$ may vary as follows:

$R_1$ hydrogen, $C_1-C_6$ alkyl, $C_2-C_6$ alkenyl, phenyl, substituted phenyl, phenyl($C_1-C_6$ alkyl), heterocyclyl, or a group $BSO_nA$— wherein n is 0. 1 or 2 and B is hydrogen or a ($C_1-C_6$)alkyl, phenyl, substituted phenyl, heterocyclyl, $C_1-C_5$ acyl, phenacyl or substituted phenacyl group, and A represents $C_1-C_6$ alkyl, amino; protected amino; acylamino; OH; SH; $C_1-C_6$ alkoxy; $C_1-C_6$ alkylamino; $C_1-C_6$ alkylthio; aryl ($C_1-C_6$ alkyl); amino($C_1-C_6$ alkyl); hydroxy($C_1-C_6$ alkyl), mercapto($C_1-C_6$ alkyl) or carboxy($C_1-C_6$ alkyl) wherein the amino-, hydroxy-, mercapto- or carboxyl- group are optionally protected or the carboxyl- group amidated; lower alkyl substituted by maleimido, succinimido, naphthalimido, 2,3-dihydro-1,3-dioxo-1H-benz[d,e]isoquinol-2-yl, carbamoyl, mono(lower alkyl)carbamoyl, di(lower alkyl)carbamoyl, di(lower alkyl)amino, carboxy-lower alkanoylamino, pyrrolidino or morpholino;

$R_2$ ($C_1-C_{)alkyl;}$ $(C_2-C_6)$alkenyl; phenyl($C_1-C_6$)alkyl; cycloalkyl ($C_1C_6$)alkyl; cycloalkenyl ($C_1-C_6$)alkyl; substituted amino; carboxyl; esterified carboxyl; or a group —Y—X—Z wherein Y is a single bond or ($C_1-C_6$)alkylene. X is O or S, and Z is ($C_1-C_6$)alkyl;

$R_3$ $C_1-C_6$ alkyl; benzyl; benzyloxybenzyl; ($C_1-C_6$ alkoxy)benzyl; benzyloxy($C_1-C_6$ alkyl); the characterising group of a natural α amino acid, which may be protected if functional groups are present, eg by acylation of amino groups and amidation of carboxyl groups; a group —[Alk]$_n$R$^6$ where Alk is an $C_1-C_6$ alkyl or $C_2-C_6$ alkenyl group optionally interrupted by one or more —O—, or —S— atoms or —N(R$^7$)- groups [where R$^7$ is a hydrogen atom or a $C_1-C_6$ alkyl group], n is 0 or 1, and R$^6$ is an optionally substituted cycloalkyl or cycloalkenyl group; a benzyl group with one or two substituents in the phenyl ring selected from hydrogen, halogen, cyano amino, amino ($C_1-C_6$)alkyl, amino di ($C_1-C_6$)alkyl, amino ($C_1-C_6$)alkylacyl, aminophenacyl, amino(substituted)phenacyl, amino acid or derivative thereof, hydroxy, oxy ($C_1-C_6$)alkyl, oxyacyl, formyl, carboxylic acid, carboxamide, carboxy ($C_1-C_6$)alkylamide, carboxyphenylamide, carboxy ($C_1-C_6$)alkyl, hydroxy ($C_1-C_6$)alkyl, ($C_1-C_6$) alkyloxy ($C_1-C_6$)alkyl or acyloxy ($C_1-C_6$)alkyl, ($C_1-C_6$)alkylcarboxylic acid, or ($C_1-C_6$)alkylcarboxy ($C_1-C_6$)alkyl, amino($C_1-C_6$)alkylacyl carboxylic acid or amino($C_1-C_6$)alkylcarboxylate; or a benzyl group with one substituent in the phenyl ring selected from groups of formula —OCH$_2$CN, —OCH$_2$COR$^8$ and —OCH$_2$CH$_2$OR$^9$, where R$^8$ is hydroxyl, ($C_1-C_6$) oxyalkyl, ($C_1-C_6$)oxyalkylphenyl, amino, ($C_1-C_6$) aminoalkyl, ($C_1-C_6$)aminodialkyl, ($C_1-C_6$) aminoalkylphenyl, an amino acid or derivative thereof; and R$^9$ is ($C_1-C_6$)alkyl, ($C_1-C_6$)alkylphenyl, phenyl, substituted phenyl ($C_1-C_6$)alkylacyl or phenacyl; heterocyclic lower alkyl, either being unsubstituted or mono- or di-substituted with halo, nitro, carboxy, $C_1-C_6$ alkoxy, cyano, $C_1-C_6$ alkanoyl, trifluoromethyl $C_1-C_6$ alkyl, hydroxy, formyl, amino, $C_1-C_6$ alkyl amino, di-$C_1-C_6$ alkyl amino, mercapto, $C_1-C_6$ alkylthio, or mercapto $C_1-C_6$ alkyl; $C_1-C_6$ alkyl) phenylmethyl;

$R_4$ hydrogen, $C_1-C_6$ alkyl; a group —CHBD wherein B is H and D is H or $C_1-C_6$ alkyl, $C_1-C_6$ alkoxy-$C_1-C_6$ alkyl, di($C_1-C_6$ alkoxy)methyl, carboxy, $C_1-C_6$ alkylcarbonyl, $C_1-C_6$ alkoxycarbonyl, arylmethoxycarbonyl, $C_1-C_6$ alkylaminocarbonyl or arylaminocarbonyl; or $R_3$ and B together form a group (CH$_2$)n where n is an integer from 4–11; phenyl($C_1-C_2$ alkyl), or trifluoromethylphenyl($C_1-C_2$alkyl); a group —(CH$_2$)$_n$A wherein n is an integer from 1 to 6 and A represents the group —NH$_2$, a substituted acyclic amine, a heterocyclic base, hydroxy, ($C_1-C_6$)alkoxy, ($C_2-C_7$)acyloxy, ($C_1-C_6$)alkylthio, phenylthio, ($C_2-C_7$)acylamino or an N-pyrrolidone group; an optionally substituted straight or branched alkyl group, optionally interrupted by one or more —O— or —S— atoms or —N(R$^7$)-groups [where R$^7$ is a hydrogen atom or a $C_1-C_6$ alkyl group], or aminocarbonyloxy groups; $C_1-C_6$ alkyl optionally substituted by aryl, amino, protected amino, di(lower alkyl)amino, guanidino, carboxyl, protected carboxyl, carbamoyl, mono(lower alkyl)carbamoyl, di(lower alkyl) carbamoyl, di(lower alkyl)phosphinyl, dihydroxyphosphinyl, pyrrolidino, piperidino or morpholino;

$R_5$ hydrogen;

Detailed Description of the Invention

In a first aspect of the invention there is provided the use of a compound forming part of the state of the art by virtue of any of the patent publications listed above in the preparation of an agent for use in the treatment of diseases mediated by TNF.

Without prejudice to the generality of the foregoing, the invention includes the use of a compound according to the general composite structural definition set out above in the preparation of an agent for use in the treatment of diseases mediated by TNF.

More particularly the invention includes the use of a compound according to the general composite structural definition set out above in the preparation of an agent for use in the treatment of diseases mediated by TNF.

In another aspect, this invention concerns a method of management (by which is meant treatment or prophylaxis) of diseases mediated by TNF in mammals, in particular in humans, which method comprises administering to the mammal an effective amount of a compound forming part of the state of the art by virtue of any of the patent publications listed above.

Without prejudice to the generality of the foregoing, the invention includes a method of management (by which is meant treatment or prophylaxis) of diseases mediated by TNF in mammals, in particular in humans, which method comprises administering to the mammal an effective amount-of a compound according to the general composite structural definition set out above.

More particularly, the invention includes a method of management (by which is meant treatment or prophylaxis) of diseases mediated by TNF in mammals, in particular in humans, which method comprises administering to the mammal an effective amount of a a compound according to the reduced composite structural definition set out above.

Diseases mediated by TNF include, but are not limited to, inflammation, fever, cardiovascular effects, haemmorhage, coagulation and acute phase response, cachexia and anorexia, acute infections, shock states, graft versus host reactions and autoimmune disease.

Specifically the target for the present invention is inhibition of the release of and the effects of TNF in septic shock, haemodynamic shock or sepsis syndrome, in post ischaemic reperfusion injury, in malaria, mycobacterial infection and meningitis, in psoriasis, in cancer, in cachexia, in fibrotic disease, in congestive heart failure, in graft rejection, in rheumatoid arthritis, in radiation damage and toxicity following administration of immunosuppressive monoclonal antibodies such as OKT3 or CAMPATH-1, in hyperoxic alveolar injury, in autoimmune disease for example AIDS and multiple sclerosis, and in any disease state where TNF is a mediator of host injury.

Specific compounds having TNF inhibitory activity, for use in the present invention are those listed in the Examples below, particularly those listed in Example 2, Group A.

The compounds with which the invention is concerned may be prepared for administration by any route consistent with their physicochemical and pharmacokinetic properties. The compositions thus may be in the form of tablets, capsules, powders, granules, lozenges, liquid or gel preparations, such as oral, topical, or sterile parenteral solutions or suspensions, as appropriate. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents for example lecithin, sorbitan monooleate, or acacia; non-aqueous vehicles (which may include edible oils), for example almond oil, fractionated coconut oily esters such as glycerine, propylene glycol, or ethyl alcohol; preservatives for example methyl or propyl p-hydroxybenzoate or sorbic acid, and if desired conventional flavouring or colouring agents.

The dosage unit for oral administration may contain from about 1 to 250 mg for example from about 25 to 250 mg of a compound of general formula I. A suitable daily dose for a mammal may vary widely depending on the condition of the patient. However, a dose of a compound of general formula I of about, 0.1 to 300 mg/kg body weight, particularly from about 1 to 100 mg/kg body weight may be appropriate.

For topical application to the skin, the drug may be made up into a cream lotion or ointment. Cream or ointment formulations which may be used for the drug are conventional formulations well known in the art, for example as described standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetates or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Although this invention is concerned with the use of certain matrix metalloproteinase inhibitors containing a hydroxamic acid group, known from specific patent publications as described above, it is thought highly probable that those other structural classes of compounds which are known in the art as matrix metalloproteinase inhibitors will, by analogous mechanisms, also have the property of inhibiting the production of TNF, and will therefore also be of use for the treatment of TNF-mediated diseases.

The following examples illustrate the invention, but are not intended to limit the scope in any way. As stated, the known MMP inhibitors made part of the state of the art by virtue of the patent publications listed above have in general the property of inhibiting TNF production, although of course the potency of the compounds in vitro and in vivo will vary. Compounds which on first testing appear less active, may nonetheless show higher potencies when optimally formulated or when administered at higher dose levels, or when the dosage schedule is optimised.

EXAMPLE 1

Metalloproteinase inhibitors can prevent the release of TNF from PMA-stimulated human monocytic cell line U937.

The ability of representative compounds, which are inhibitors of metalloproteinases, to inhibit the release of TNF was investigated. The assay is based on the ability of phorbol myristate acetate (PMA) to stimulate the release of TNFα from a human monocytic cell line, U937.

U937 cells cultured in RPMI 1640 medium +5% foetal calf serum were centrifuged at 1000×g for 5 minutes and then resuspended in medium at $2 \times 10^6$/ml. 1 ml of cell suspension was aliquoted into individual wells of 24-well plates. Test compounds were dissolved in dimethyl sulphoxide (DMSO) at a stock concentration of 100 mM, then diluted to 50×the final required concentration with RPMI 1640 medium. 20 μl of the diluted compounds were added to U937 cells in duplicate wells. TNFα release was stimulated by addition of PMA to the cells at a final concentration of 50 nM. Appropriate control cultures were set up in duplicate. The plates were incubated for 18 hours at 37° C., 5% $CO_2$, then centrifuged at 1000 ×g for 5 minutes. A specific ELISA for TNFα obtained from British Biotechnology Products Limited, Abingdon, England was used to measure TNFα levels in the culture supernatants according to the protocol supplied.

The average concentration of test compound which inhibits the release of TNFα by 50% relative to the control culture was assessed as greater than 90 μM, in the range 10 μM–90 μM, or less than 10 μM.

Group A: Compounds with $IC_{50}$s less than 10 micromolar.

1. 3R-(2-(4-methoxyphenyl)-1S-methylcarbamoyl-ethylcarbamoyl)-2S,5-dimethyl-hexanohydroxamic acid,
2. 2S-(phenylsulfanylmethyl)-3R-(2-phenyl-1S-methylcarbamoyl-ethylcarbamoyl)-5-methyl-hexanohydroxamic acid.
3. 2S-(thien-2-ylsulfanylmethyl)-3R-(2-phenyl-1S-methylcarbamoyl-ethylcarbamoyl)-5-methyl-hexanohydroxamic acid.
4. 2S-(benzoylsulfanylmethyl)-3R-(2-phenyl-1S-methylcarbamoyl-ethylcarbamoyl)-5-methyl-hexanohydroxamic acid.
5. 3R-{2-phenyl-1S-(3-[2-oxo-pyrolidin-1-yl]propylcarbamoyl)-ethylcarbamoyl}-2S,5-dimethyl-hexanohydroxamic acid.
6. 3R-(2-phenyl-1S-(2-[pyrid-2yl]ethyl)carbamoyl-ethylcarbamoyl)-2S,5-dimethyl-hexanohydroxamic acid hydrochloride.
7. 2S-(2,2-dimethylpropionylsulfanylmethyl)-3R-(2-phenyl-1S-methylcarbamoyl-ethylcarbamoyl)-5-methyl-hexanohydroxamic acid.
8. 3R-(2-phenyl-1S-pyrid-3-ylmethylcarbamoyl-ethylcarbamoyl)-2S,5-dimethyl-hexanohydroxamic acid.
9. 2S-(phenylsulfonylmethyl)-3R-(2-phenyl-1S-methylcarbamoyl-ethylcarbamoyl)-5-methyl-hexanohydroxamic acid.
10. 3R-(2-(4-methoxyphenyl)-1S-(2-hydroxyethylcarbamoyl)-ethylcarbamoyl)-2S,5-dimethyl-hexanohydroxamic acid.
11. 2S-(4-methoxyphenylsulfanylmethyl)-3R-(2-phenyl-1S-methylcarbamoyl-ethylcarbamoyl)-5-methyl-hexanohydroxamic acid.
12. sodium 2S-methyl-3R-(2-phenyl-1S-(pyrid-3-ylmethylcarbamoyl)-ethylcarbamoyl)-5-methyl-hexanohydroxamate.
13. 2S-(3-bromophenylsulfanylmethyl)-3R-(2-phenyl-1S-methylcarbamoyl-ethylcarbamoyl)-5-methyl-hexanohydroxamic acid.
14. sodium 2S-methyl-3R-(2-phenyl-1S-(pyrid-4-ylmethylcarbamoyl)-ethylcarbamoyl)-5-methyl-hexanohydroxamate.
15. 2S-(4-hydroxyphenylsulfanylmethyl)-3R-(2-phenyl-1S-methylcarbamoyl-ethylcarbamoyl)-5-methyl-hexanohydroxamic acid.
16. 2S-(3-chlorophenylsulfanylmethyl)-3R-(2-phenyl-1S-methylcarbamoyl-ethylcarbamoyl)-5-methyl-hexanohydroxamic acid.
17. 2S-(phenylsulfanylmethyl)-3R-(2-phenyl-1S-(pyrid-3-ylmethylcarbamoyl)-ethylcarbamoyl)-5-methyl-hexanohydroxamic acid.
18. 2S-(3-methylphenylsulfanylmethyl)-3R-(2-phenyl-1S-methylcarbamoyl-ethylcarbamoyl)-5-methyl-hexanohydroxamic acid.
19. 2S-(4-acetamidophenylsulfanylmethyl)-3R-(2-phenyl-1S-methylcarbamoyl-ethylcarbamoyl)-5-methyl-hexanohydroxamic acid.
20. 2S-(thien-2-ylsulfanylmethyl)-3R-(2-(4-methoxyphenyl)-1S-methylcarbamoyl-ethylcarbamoyl)-5-methyl-hexanohydroxamic acid,
21. 2S-(4-[3-ethoxycarbonyl-propionylamino]phenylsulfanylmethyl)-3R-2-phenyl-1S-methylcarbamoyl-ethylcarbamoyl)-5-methyl-hexanohydroxamic acid.
22. 2S-(methoxycarbonylmethylsulfanylmethyl)-3R-(2-phenyl-1S-methylcarbamoyl-ethylcarbamoyl)-5-methyl-hexanohydroxamic acid.
23. 3R-(2-(4-acetamidophenyl)-1S-methylcarbamoyl-ethylcarbamoyl)-5-methyl-hexanohydroxamic acid.
24. 3R-(2-(4-dimethylcarbamoylmethoxyphenyl)-1S-methylcarbamoyl-ethylcarbamoyl)-5-methyl-hexanohydroxamic acid.
25. 2S-(thien-2-ylsulfanylmethyl)-3R-(3-methoxycarbonyl-1S-methylcarbamoyl-propylcarbamoyl)-5-methyl-hexanohydroxamic acid.
26. dilithio-2S-methyl-3R-(2-(4-carboxymethylcarbamoylmethoxyphenyl)-1S-methylcarbamoyl-ethylcarbamoyl)-5-methyl-hexanohydroxamate.
27. dilithio-2S-(thien-2-ylsulphanylmethyl)-3R-(2-(4-carboxymethylcarbamoylmethoxyphenyl)-1S-methylcarbamoyl-ethylcarbamoyl)-5-methyl-hexanohydroxamate.
28. 2S-(thien-2-ylsulphanylmethyl)-3R-(2-(4-methoxycarbonylmethoxyphenyl)-1S-methylcarbamoyl-ethylcarbamoyl)-5-methyl-hexanohydroxamic acid.
29. 2S-(thien-2-ylsulphanylmethyl)-3R-(2-(4-carboxymethoxyphenyl)-1S-methylcarbamoyl-ethylcarbamoyl)-5-methyl-hexanohydroxamic acid.
30. 2S-(thien-2-ylsulphanylmethyl)-3R-(5-(1,1-dimethyl-ethoxycarbamoyl)-1S-methylcarbamoyl-pentylcarbamoyl)-5-methyl-hexanohydroxamic acid.
31. 2S-(thien-2-ylsulphanylmethyl)-3R-(2-phenyl-1S-(pyrid-3-ylmethylcarbamoyl)-ethylcarbamoyl)-5-methyl-hexanohydroxamic acid.
32. 2S-(4-hydroxyphenylsulphanylmethyl)-3R-(5-(1,1-dimethyl-ethoxycarbamoyl)-1S-methylcarbamoyl-pentylcarbamoyl)-5-methyl-hexanohydroxamic acid.
33. 3R-(5-(1,1-dimethyl-ethoxycarbamoyl)-1S-methylcarbamoyl-pentylcarbamoyl)-2S,5-dimethyl-hexanohydroxamic acid.
34. 2S-(4-hydroxyphenylsulphanylmethyl)-3R-(2-phenyl-1S-(pyrid-3-ylmethylcarbamoyl)-ethylcarbamoyl)-5-methyl-hexanohydroxamic acid.
35. 2S-(4-aminophenylsulphanylmethyl)-3R-(2-phenyl-1S-(pyrid-3-ylmethylcarbamoyl)-ethylcarbamoyl)-5-methyl-hexanohydroxamic acid.
36. 2S-(methoxycarbonylmethylsulphanylmethyl)-3R-(2-phenyl-1S-(pyrid-3-ylmethylcarbamoyl)-ethylcarbamoyl)-5-methyl-hexanohydroxamic acid.
37. Dilithio-2S-(thien-2-ylsulphanylmethyl)-3R-(2-(4-[3-carboxypropionyl]amino-phenyl)-1S-methylcarbamoyl-ethylcarbamoyl)-5-methyl-hexanohydroxamate.
38. Dilithio-2S-(4-aminophenylsulphanylmethyl)-3R-(2-[4-{3-carboxypropionyl}amino-phenyl]-1S-methylcarbamoyl-ethylcarbamoyl)-5-methyl-hexanohydroxamate.
39. Dilithio-2S-(4-hydroxyphenylsulphanylmethyl)-3R-(2-[4{3-carboxypropionyl}amino-phenyl]-1S-methylcarbamoyl-ethylcarbamoyl)-5-methyl-hexanohydroxamate.
40. 2S-hydroxy-3R-(2-phenyl-1S-methylcarbamoyl-ethylcarbamoyl)-5-methyl-hexanohydroxamic acid.
41. 2R-(3-bromophenylmethyl)-3R-(2-phenyl-1S-methylcarbamoyl-ethylcarbamoyl)-5-methyl-hexanohydroxamic acid.

42 2R-(3-bromophenylmethyl)-3R-(3-methoxycarbonyl-1S-methylcarbamoyl-propylcarbamoyl)-5-methyl-hexanohydroxamic acid.

43 2S-(4-hydroxyphenylsulphanylmethyl)-3R-(5-[1,1-dimethyl-ethoxycarbonyl], [4-hydroxyphenylsulfanylmethyl]-amino-1S-methylcarbamoyl-pentylcarbamoyl)-5-methyl-hexanohydroxamic acid.

44 2S-(thien-2-ylsulfanylmethyl)-3R-(2-naph-2-yl-1S-methylcarbamoyl-ethylcarbamoyl)-5-methyl-hexanohydroxamic acid.

45 2S-(3,4-dimethoxyphenylsulfanylmethyl)-3R-(2-phenyl-1S-methylcarbamoyl-ethylcarbamoyl)-5-methyl-hexanohydroxamic acid.

46 2S-(4-[thien-2-yl]acetamidophenylsulfanylmethyl)-3R-(2-phenyl-1S-methylcarbamoyl-ethylcarbamoyl)-5-methyl-hexanohydroxamic acid.

47 2S-hydroxy-3R-(2-oxo-aza-tridecan-3-ylcarbamoyl)-5-methyl-hexanohydroxamic acid.

48 2S-(thien-2-ylsulfanylmethyl)-3R-(2-phenyl-1S-[2,2-dimethylpropionyloxymethyl]-methyl-carbamoyl-ethylcarbamoyl)-5-methyl-hexanohydroxamic acid.

49 2S-(4-hydroxyphenylsulfanylmethyl)-3R-(2R-hydroxy-1S-methylcarbamoyl-propylcarbamoyl)-5-methyl-hexanohydroxamic acid.

50 2S-(4-hydroxyphenylsulfanylmethyl)-3R-(5-acetamido-1S-methylcarbamoyl-pentylcarbamoyl)-5-methyl-hexanohydroxamic acid.

51 2S-(ethylsulfanylmethyl)-3R-(2-cyclohexyl-1S-methylcarbamoyl- ethylcarbamoyl)-5-methyl-hexanohydroxamic acid.

52 2S-(4-hydroxyphenylsulfanylmethyl)-3R-(2-[1,1-dimethylethoxycarbonyl]-1S-methylcarbamoyl-ethylcarbamoyl)-5-methyl-hexanohydroxamic acid.

53 2S-(4-hydroxyphenylsulfanylmethyl)-3R-(3-methoxycarbonyl-1S-methylcarbamoyl-propylcarbamoyl)-5-methyl-hexanohydroxamic acid.

54 2S-(4-hydroxyphenylsulfanylmethyl)-3R-(3-[1,1-dimethylethoxycarbonyl]-1S-methylcarbamoyl-propylcarbamoyl)-5-methyl-hexanohydroxamic acid.

55 2S-(ethylsulfanylmethyl)-3R-(3-methoxycarbonyl-1S-methylcarbamoyl-propylcarbamoyl)-5-methyl-hexanohydroxamic acid.

56 2S-(4-aminophenylsulfanylmethyl)-3R-(3-methoxycarbonyl-1S-methylcarbamoyl-propylcarbamoyl)-5-methyl-hexanohydroxamic acid.

57 2S-(4-methoxyphenylsulfanylmethyl)-3R-(3-methoxycarbonyl-1S-methylcarbamoyl-propylcarbamoyl)-5-methyl-hexanohydroxamic acid.

58 2S-(benzylsulfanylmethyl)-3R-(3-methoxycarbonyl-1S-methylcarbamoyl-propylcarbamoyl)-5-methyl-hexanohydroxamic acid.

59 2S-(benzyloxy)-3R-(2-phenyl-1S-methylcarbamoyl-ethylcarbamoyl)-5-methyl-hexanohydroxamic acid.

60 2S-(4-hydroxyphenylsulfanylmethyl)-3R-(3-carboxy-1S-methylcarbamoyl-propylcarbamoyl)-5-methyl-hexanohydroxamic acid.

61 2S-(1,1-dimethylethylsulfanylmethyl)-3R-(3-methoxycarbonyl-1S-methylcarbamoyl-propylcarbamoyl)- 5-methyl-hexanohydroxamic acid.

62 2S-(prop-2-enyloxy)-3R-(2-phenyl-1S-methylcarbamoyl-ethylcarbamoyl)-5-methyl-hexanohydroxamic acid.

63 2S-hydroxy-3R-(3-methoxycarbonyl-1S-methylcarbamoyl-propylcarbamoyl)-5-methyl-hexanohydroxamic acid.

64 2S-(prop-2-enyloxy)-3R-(2-cyclohexyl-1S-methylcarbamoyl-ethylcarbamoyl)-5-methyl-hexanohydroxamic acid.

65 2S-(4-hydroxyphenylsulfanylmethyl)-3R-(3-methylcarbamoyl-1S-methylcarbamoyl-propylcarbamoyl)-5-methyl-hexanohydroxamic acid.

66 2S-(4-hydroxyphenylsulfanylmethyl)-3R-(2-phenyl-1S-methylcarbamoyl-ethylcarbamoyl)-4-methyl-pentanohydroxamic acid.

67 3R-(2-phenyl-1S-[1-hydroxy-2,2-dimethyl-prop-3-yl] carbamoyl-ethylcarbamoyl)-5-methyl-hexanohydroxamic acid.

68 2-(1S-formylhydroxyamino-butyl)-4-methyl-pentanoic acid-[1-(1S-methylcarbamoyl)-2-{4-methoxyphenyl}-ethyl]-amide Group B: Compounds with IC$_{50}$s between 10 and 90 micromolar.

69 3S-(2(4-methoxyphenyl)-1S-methylcarbamoyl-ethylcarbamoyl)-2S,5-dimethyl-hexanohydroxamic acid.

70 3R-(2(4-methoxyphenyl)-1S-methylcarbamoyl-ethylcarbamoyl)-5-methyl-hexanohydroxamic acid.

71 3R-(2-phenyl-1S-carboxy-ethylcarbamoyl)-5-methyl-hexanohydroxamic acid.

72 3R-(2-phenyl-1S-[3-imidazo-1-yl-]propylcarbamoyl-ethylcarbamoyl)-5-methyl-hexanohydroxamic acid.

73 3R-(2-phenyl-1S-[2-(1-methylpyrrol-2-yl) ethylcarbamoyl]-ethylcarbamoyl)-5-methyl-hexanohydroxamic acid.

74 3R-(2-phenyl-1S-[2-oxo-pyrolid-1-yl] propylcarbamoyl-ethylcarbamoyl)-5-methyl-hexanohydroxamic acid.

75 2S-(2,4-dimethylphenylsulfanylmethyl)-3R-(2-phenyl-1S-methylcarbamoyl-ethylcarbamoyl)-5-methyl-hexanohydroxamic acid.

76 3R-(2-phenyl-1S-methylcarbamoyl-ethylcarbamoyl)-5-methyl-hexanohydroxamic acid.

77 3R-(2-[4-cyanophenyl]-1S-methylcarbamoyl-ethylcarbamoyl)-5-methyl-hexanohydroxamic acid.

78 3R-(2-[4-methoxycarbonylmethylcarbamoylmethoxyphenyl]-1S-methylcarbamoyl-ethylcarbamoyl)-5-methyl-hexanohydroxamic acid.

79 3R-(2-[4-carboxymethylcarbamoylmethoxyphenyl]-1S-methylcarbamoyl-ethylcarbamoyl)-5-methyl-hexanohydroxamic acid.

80 3R-(2-[4-carbamoylmethoxyphenyl]-1S-methylcarbamoyl-ethylcarbamoyl)-5-methyl-hexanohydroxamic acid.

81 3R-(2-[4-aminophenyl]-1S-methylcarbamoyl-ethylcarbamoyl)-5-methyl-hexanohydroxamic acid.

82 3R-(2-phenyl-1S-[2-phenyl-1R-methyl-ethylcarbamoyl]-ethylcarbamoyl)-5-methyl-hexanohydroxamic acid.

83 dilithio-3R -(2-[4-{3-carboxypropionyl}aminophenyl]-1S-methylcarbamoyl-ethylcarbamoyl)-2S,5-dimethyl-hexanohydroxamate.

84 2R-(4-hydroxyphenylsulfanylmethyl)-3R-(3-methoxycarbonyl-1S-methylcarbamoyl-propylcarbamoyl)-5-methyl-hexanohydroxamic acid.

85 3R-(2-phenyl-1S-[2-amino-ethylcarbamoyl]-ethylcarbamoyl)-5-methyl-hexanohydroxamic acid.

86 3R-(2-phenyl-1S-[3-{morpholin-4-yl}-propylcarbamoyl]-ethylcarbamoyl)-4-cyclopentylcyclopentyl-butanohydroxamic acid.

87 3R-(2-phenyl-1S-methylcarbamoyl-ethylcarbamoyl)-5-phenyl-pentanohydroxamic acid.

88 3R-(2,2-dimethyl-1S-methylcarbamoyl-propylcarbamoyl)-5-methyl-hexanohydroxamic acid.

89 2S-thiomethyl3R-(3-methoxycarbonyl-1S-methylcarbamoyl-propylcarbamoyl)-5-methyl-hexanohydroxamic acid, 90 3R-(6-carbamoyl-1S-methylcarbamoyl-hexylcarbamoyl)-5-methyl-hexanohydroxamic acid.

91 3R-(4-carbamoyl-1S-methylcarbamoyl-butylcarbamoyl)-5-methyl-hexanohydroxamic acid.

92 2S-(4-phthalimido-butyl)-3S-(3-methyl-1S-ethoxycarbonylmethylcarbamoyl-butylcarbamoyl)-5-methyl-hexanohydroxamic acid.

93 2S-(4-phthalimido-butyl)-3R-(3-methyl-1S-ethoxycarbonylmethylcarbamoyl-butylcarbamoyl)-5-methyl-hexanohydroxamic acid.

94 3R-(2-phenyl-1S-phenylcarbamoyl-ethylcarbamoyl)-5-methyl-hexanohydroxamic acid.

95 2-formylhydroxyaminomethyl-4-methyl-pentanoic acid-[1-(1S-methylcarbamoyl)-2-{4-methoxyphenyl}-ethyl]-amide 96 2-(1S-formylhydroxyamino-ethyl)-4-methyl-pentanoic acid-[1-(1S-methylcarbamoyl)-2-{4-carboxymethoxyphenyl}-ethyl]-amide 97 2-(1S-formylhydroxyamino-ethyl)-4-methyl-pentanoic acid-[1-(1S-methylcarbamoyl)-2-{4-aminophenyl}-ethyl]-amide 98 3R-(2-phenyl-1S-[pyrid-3-ylmethylcarbamoyl]-ethylcarbamoyl)-5-methyl-hexanohydroxamic acid.

99 2S-(thien-2-ylsulfonylmethyl)-3R-(2-phenyl-1S-methylcarbamoyl-ethylcarbamoyl)-5-methyl-hexanohydroxamic acid.

Group C: Compounds with $IC_{50}$s greater than 90 micromolar.

100 3R-(2-(4-methoxyphenyl)-1S-dimethylcarbamoyl-ethylcarbamoyl)-5-methyl-hexanohydroxamic acid.

101 3R-(2-oxo-1,2,3,4-tetrahydro-quinoli-3-ylcarbamoyl)-5-methyl-hexanohydroxamic acid.

102 3R-(5-amino-1S-methylcarbamoyl-pentylcarbamoyl)-5-methyl-hexanohydroxamic acid.

103 3R-(3-carboxy-1S-[1S-phenyl-ethyl]carbamoyl-propylcarbamoyl)-5-methyl-hexanohydroxamic acid.

104 3R-(2-phenyl-1S-[2-carboxyethylcarbamoyl]-ethylcarbamoyl)-5-methyl-hexanohydroxamic acid.

105 3R-(2-phenyl-1S-[2-phenyl-1S-methoxycarbonyl-ethylcarbamoyl]-ethylcarbamoyl)-5-methyl-hexanohydroxamic acid.

106 3R-(2-pyrazol-1-yl-1S-methylcarbamoyl-ethylcarbamoyl)-5-methyl-hexanohydroxamic acid.

107 3R-(2-phenyl-1R-carboxy-ethylcarbamoyl)-5-methyl-hexanohydroxamic acid.

108 3R-(3-methyl-1S-[1R-ethoxycarbonyl-ethylcarbamoyl]-butylcarbamoyl)-5-methyl-hexanohydroxamic acid.

109 2S-propyl-3R-(2-phenyl-1S-methylcarbamoyl-ethylcarbamoyl)-5-methyl-hexanohydroxamic acid.

110 3R-(2-phenyl-1S-[1,1-dimethylethylcarbamoyl]-ethylcarbamoyl)-5-methyl-hexanohydroxamic acid.

111 3R-(2-methyl-1S-methylcarbamoyl-propylcarbamoyl)-5-methyl-hexanohydroxamic acid.

112 3R-(2-phenyl-1S-[1,1-dimethyl-propylcarbamoyl]-ethylcarbamoyl)-5-methyl-hexanohydroxamic acid.

113 3R-(2-phenyl-1S-dimethylcarbamoyl-ethylcarbamoyl)-4-methyl-pentanohydroxamic acid.

114 3R-(2-phenyl-1S-[pyrid-3-ylmethylcarbamoyl]-ethylcarbamoyl)-5-methyl-hexanohydroxamic acid.

EXAMPLE 2

Metalloproteinase inhibitors can prevent the release of TNF from LPS-stimulated whole blood cultures.

The ability of representative compounds, which are inhibitors of metalloproteinases, to inhibit the release of TNF was investigated. A modified whole blood culture system was used (Wilson B. M. G., Severn A., Rapsor, N. T. Chana J. & Hopkins P. (1991) J. Immunol. Meths. 139:233–240). The compounds tested were nos 1,69, 24, 78, 2,and 34.

Blood was removed from healthy volunteers by venepuncture into heparinised containers, diluted to 1:4 with RPMI 1640 medium and aliquoted into 1.5 ml culture wells. Test compounds were added directly to each well. Control cultures containing RPMI-1640 alone, LPS at 100 ng/ml and LPS plus diluent were included in each experiment. Test compounds at dilutions from 100 µM final concentration were added to culture wells containing 100 ng/ml LPS. After 24 hrs incubation at 37° C., supernatants were removed, centrifuged at 1200 rpm for 10 mins and assayed for TNFα. A specific ELISA for TNFα (British Bio-technology Products) was used to measure TNF levels. The specificity of inhibition was confirmed by measuring the release of IL-1b and IL-6 from the same cultures using specific ELISAs (British Bio-technology Products Limited, Abingdon, England). The production of these latter cytokines was not inhibited by the metalloproteinase inhibitors.

The test compounds specifically inhibit the release of TNF from LPS-stimulated blood cells into the supernatant at concentrations below 100 µM.

EXAMPLE 3

Test compounds were assessed for their ability to inhibit release of endotoxin induced TNF production in vivo.

Male CD rats (Charles River, UK) weighing between 300 g–400 g were anaesthetised with an intra-peritoneal injection of a mixture of 62.5 mg.kg$^{-1}$ thiopental and 22.5 mg.kg$^{-1}$ sodium pentobarbitone (Thiopental, Sigma Chemical Co., UK; Sodium pentobarbitone (Sagatal), May and Baker., UK). The trachea was exposed and cannulated to allow spontaneous respiration through a patent airway. The left jugular vein was exposed and cannulated for the administration of LPS. The right femoral artery was exposed and cannulated for withdrawal of blood samples. Blood samples (1 ml) were removed 5 minutes prior to bolus administration of either LPS (*E. coil* serotype 0111:b$_4$, Difco Laboratories, USA) or saline (NaCL 0.9% w/v) and at intervals of 1 hour and 2 hours after LPS. Removed blood was replaced with equal amounts of saline.

Rats were administered LPS at a dose of 5001 µg.kg$^{-1}$ which resulted in a marked increase in TNF α levels in comparison to saline controls. The peak of TNF release was at the 1 hour timepoint. TNF levels were expressed in units/ml where 1 unit is the equivalent of 1 pg of mouse TNF α.

Rat serum TNF levels were measured using a mouse TNF α reference standard. The commercial ELISA kits were from Genzyme.

Test compounds were administered intraperitoneally to anaesthetised rats at a dose of 10 mg.kg$^{-1}$, 1 hour prior to LPS administration.

The results are expressed as the % inhibition of maximal TNF elevation relative to control:

| Compound Tested | % Inhibition of Maximal TNF Elevation |
|---|---|
| 87 | 4 |
| 99 | 55 |
| 23 | 35 |
| 93 | 43 |
| 1 | 0 |
| 74 | 28 |
| 70 | 37 |
| 98 | 28 |
| 88 | 66 |

In a variation of the above methodology, the infusion of compound 29,1 mg/kg/hr, 15 minutes prior to the administration of LPS, 500 μg.kg$^{-1}$, for 2 hours resulted in a 60% inhibition of maximal TNF elevation relative to control.

We claim:

1. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

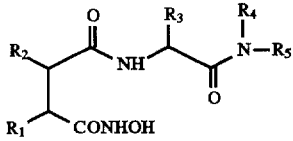

wherein the five substituents $R_1$–$R_5$ may vary as follows:

$R_1$ hydrogen, $C_1$–$C_6$ alkyl, phenyl, phenyl($C_1$–$C_6$ alkyl);

$R_2$ hydrogen, phenyl, phenyl($C_1$–$C_6$ alkyl), cycloalkyl, cycloalkyl($C_1$–$C_6$ alkyl);

$R_3$ $C_1$–$C_6$ alkyl, benzyl, benzyloxybenzyl, ($C_1$–$C_6$ alkoxy)benzyl, benzyloxy($C_1$–$C_6$alkyl);

$R_4$ $C_1$–$C_6$alkyl;

$R_5$ hydrogen.

2. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I) or formula (Ib):

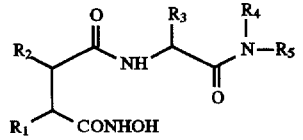

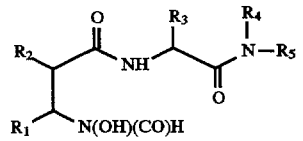

wherein the five substituents $R_1$–$R_5$ may vary as follows:

$R_1$ hydrogen, $NH_2$, OH, SH, $C_1$–$C_6$ alkyl, $C_1$–$C_6$ alkoxy, $C_1$–$C_6$ alkylamino, $C_1$–$C_6$ alkylthio or aryl($C_1$–$C_6$ alkyl) group or amino-$C_1$–$C_6$alkyl, hydroxy-$C_1$–$C_6$ alkyl, mercapto-$C_1$–$C_6$ alkyl or carboxy-$C_1$–$C_6$ alkyl;

$R_2$ $C_2$–$C_5$ alkyl;

$R_3$ the characteristic side chain a natural α amino acid, with the proviso that $R_3$ is not H or methyl;

$R_4$ a group —CHBD wherein B is H or methyl and D is H or $C_1$–$C_6$ alkyl, $C_1$–$C_6$alkoxy, $C_1$–$C_6$ alkyl, di($C_1$–$C_6$ alkoxy)methyl, carboxy, $C_1$–$C_6$ alkylcarbonyl, $C_1$–$C_6$ alkoxycarbonyl, arylmethoxycarbonyl, $C_1$–$C_5$ alkylaminocarbonyl or arylaminocarbonyl, or B and D together form a trimethylene group; or $R_3$ and B together form a group $(CH_2)_n$ where n is an integer from 4–11;

$R_5$ H or methyl.

3. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

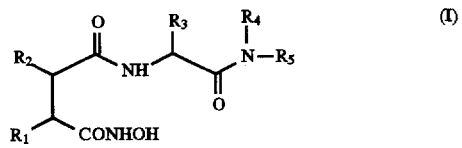

wherein the five substituents $R_1$–$R_5$ may vary as follows:

$R_1$ hydrogen;

$R_2$ isobutyl;

$R_3$ isopropyl, 4-aminobutyl, n-butyl, 2-methylmercaptoethyl;

$R_4$ hydrogen, phenyl($C_1$–$C_2$ alkyl), or trifluoromethylphenyl($C_1$–$C_2$ alkyl);

$R_5$ hydrogen.

4. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

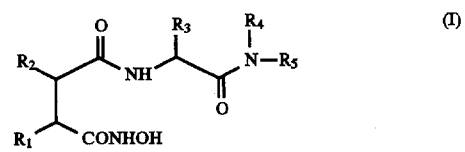

wherein the five substituents $R_1$–$R_5$ may vary as follows:

$R_1$ hydrogen, $C_1$–$C_6$ alkyl, $C_2$–$C_6$ alkenyl, phenyl, phenyl ($C_1$–$C_6$ alkyl), or a group $BSO_nCH_2$-wherein n is 0, 1 or 2 and B is hydrogen or a ($C_1$–$C_6$) alkyl, phenyl, substituted phenyl, phenyl($C_1$–$C_6$)alkyl, or heterocyclyl group;

$R_2$hydrogen atom or an ($C_1$–$C_6$)alkyl, ($C_2$–$C_6$)alkenyl, phenyl($C_1$–$C_6$)alkyl, cycloalkyl ($C_1$–$C_6$)alkyl or cycloalkenyl ($C_1$–$C_6$)alkyl group;

$R_3$ an amino acid residue or a ($C_1$–$C_6$)alkyl, benzyl, ($C_1$–$C_6$) alkoxy benzyl or benzyloxy ($C_1$–$C_6$) alkyl group;

$R_4$a group —$(CH_2)_n$A wherein n is an integer from 1 to 6 and A represents the group —$NH_2$, a substituted acyclic amine or a heterocyclic base;

$R_5$ a hydrogen atom or a methyl group.

5. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

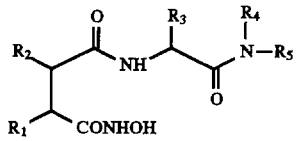

wherein the five substituents $R_1$–$R_5$ may vary as follows:

$R_1$ a group $BSO_nA$-wherein n is 0, 1 or 2 and B is hydrogen or an alkyl, phenyl, phenylalkyl, heterocyclyl, alkylcarbonyl or phenacyl, and A represents a hydrocarbon chain optionally substituted with one or more alkyl or phenyl groups;

$R_2$ a hydrogen atom or an alkyl, alkenyl, phenylalkyl, cycloalkylalkyl or cycloalkenylalkyl group;

$R_3$ an amino acid residue or a ($C_1$–$C_6$)alkyl, benzyl, ($C_1$–$C_6$ alkoxy) benzyl or benzyloxy ($C_1$–$C_6$alkyl) group;

$R_4$ a hydrogen atom or an alkyl group;

$R_5$ a hydrogen atom or a methyl group.

6. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

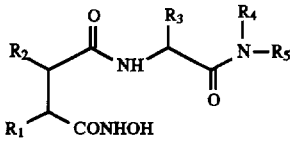

wherein the five substituents $R_1$–$R_5$ may vary as follows:

$R_1$ hydrogen or a ($C_1$–$C_6$) alkyl, ($C_2$–$C_6$) alkenyl, phenyl, phenyl ($C_1$–$C_6$)alkyl, ($C_1$–$C_6$)alkylthiomethyl, phenylthiomethyl, phenyl($C_1$–$C_6$)alkylthiomethyl or heterocyclylthiomethyl group;

$R_2$ a hydrogen atom or an ($C_1$–$C_6$)alkyl, ($C_2$–$C_6$)alkenyl, phenyl($C_1$–$C_6$)alkyl, cycloalkyl ($C_1$–$C_6$)alkyl or cycloalkenyl ($C_1$–$C_6$)alkyl group;

$R_3$ an amino acid residue or a ($C_1$–$C_6$)alkyl, benzyl, ($C_1$–$C_6$)alkoxy benzyl, benzyloxy ($C_1$–$C_6$)alkyl or benzyloxybenzyl group;

$R_4$ a group $(CH_2)_nA$ wherein n is an integer from 1 to 6 and A represents a hydroxy, ($C_1$–$C_6$)alkoxy, ($C_2$–$C_7$) acyloxy, ($C_1$–$C_6$)alkylthio, phenylthio, ($C_2$–$C_7$) acylamino or N-pyrrolidone group;

$R_5$ a hydrogen atom or a methyl group.

7. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

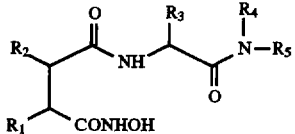

wherein the five substituents $R_1$–$R_5$ may vary as follows:

$R_1$ an alkyl, alkenyl, aryl, aralkyl, heteroalkyl, or heteroarylthioalkyl;

$R_2$ an alkyl, alkenyl, cycloalkyl, aryl, aralkyl, aralkoxy, or aralkylthio group, or an amino, substituted amino, carboxyl, or esterified carboxyl group;

$R_3$ a group -[Alk]$_n$R$^6$ where Alk is an alkenyl group optionally interrupted by one or more —O—, or —S— atoms or —N(R$^7$)-groups, where R$^7$ is a hydrogen atom or a $C_1$–$C_6$ alkyl group, n is zero or an integer 1, and R$^6$ is a cycloalkyl or cycloalkenyl group;

$R_4$ a hydrogen atom, a straight or branched alkyl group, optionally interrupted by one or more —O— or —S— atoms or —N(R$^7$)-groups (where R$^7$ is a hydrogen atom or a $C_1$–$C_6$ alkyl group), or aminocarbonyloxy groups; or R$^4$ and R$^5$ together with the nitrogen atom to which they are attached may form a $C_3$–$C_6$ cyclic amino group optionally possessing one or more other heteroatoms selected from —O— or —S— or —N(R$^7$) -groups (where R$^7$ is a hydrogen atom or a $C_1$–$C_6$alkyl group);

$R_5$ a hydrogen atom, a straight or branched alkyl group, optionally interrupted by one or more —O— or —S— atoms or —N(R$^7$)-groups (where R$^7$ is a hydrogen atom or a $C_1$–$C_6$ alkyl group), or aminocarbonyloxy groups.

8. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

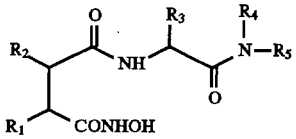

wherein the five substituents $R_1$–$R_5$ may vary as follows:

$R_1$ an alkyl, alkenyl, aryl, aralkyl, heteroalkyl, or heteroarylthioalkyl;

$R_2$ a phenylethyl, phenylpropyl or phenylbutyl group;

$R_3$ an alkyl or alkenyl group optionally interrupted by one or more —O—, or —S— atoms or —N(R$^7$)-groups (where R$^7$ is a hydrogen atom or a $C_1$–$C_6$ alkyl group;

$R_4$ a hydrogen atom, a substituted straight or branched alkyl group, optionally interrupted by one or more —O— or —S— atoms or —N(R$^7$)-groups (where R$^7$ is a hydrogen atom or a $C_1$–$C_6$ alkyl group), or aminocarbonyloxy groups; or R$^4$ and R$^5$ together with the nitrogen atom to which they are attached may form a substituted $C_3$–$C_6$ cyclic amino group optionally possessing one or more other heteroatoms selected from —O— or —S— or —N(R$^7$)-groups (where R$^7$ is a hydrogen atom or a $C_1$–$C_6$alkyl group);

$R_5$ a hydrogen atom, a substituted straight or branched alkyl group, optionally interrupted by one or more —O— or —S— atoms or —N(R$^7$)-groups (where R$^7$ is a hydrogen atom or a $C_1$–$C_6$ alkyl group), or aminocarbonyloxy groups.

9. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

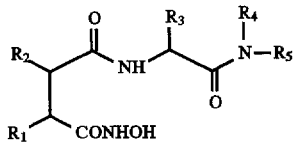

wherein the five substituents $R_1$–$R_5$ may vary as follows:

$R_1$ hydrogen, amino, acylamino, or lower alkyl optionally substituted by aryl, hydroxy, protected hydroxy, amino, protected amino, acylamino, maleimido, succinimido, naphthalimido, 2,3-dihydro-1,3-dioxo-1H-benz[d,e]isoquinol-2-yl, carboxy, carbamoyl, mono(lower alkyl) carbamoyl, di(lower alkyl)carbamoyl, di(lower alkyl) amino, carboxy-lower alkanoylamino, pyrrolidino or morpholino;

$R_2$ isobutyl;

$R_3$ tert-butyl;

$R_4$ hydrogen or lower alkyl optionally substituted by aryl, amino, di(lower alkyl)amino, guanidino, carboxyl, carbamoyl, mono(lower alkyl)carbamoyl, di(lower alkyl)carbamoyl, di(lower alkyl)phosphinyl, dihydroxyphosphinyl, pyrrolidino, piperidino or morpholino;

$R_5$ hydrogen.

10. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

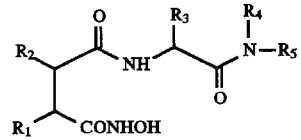

wherein the five substituents $R_1$–$R_5$ may vary as follows:

$R_1$ hydrogen ($C_1$–$C_6$) alkyl, phenyl, phenyl($C_1$–$C_6$)alkyl, or heterocyclyl; or $R^1$ represents $ASO_nR^7$ wherein A represents a ($C_1$–$C_6$) hydrocarbon chain, optionally substituted with one or more ($C_1$–$C_6$)alkyl, phenyl and n=0, 1 or 2; $R^7$ is ($C_1$–$C_6$)alkyl, phenyl, phenyl ($C_1$–$C_6$) alkyl, heterocyclyl, ($C_1$–$C_6$) alkyl, ($C_1$–$C_6$)acyl, thienyl or phenacyl;

$R_2$ hydrogen or an ($C_1$–$C_6$)alkyl, ($C_2$–$C_6$)alkenyl, phenyl ($C_1$–$C_6$)alkyl, or cycloalkyl($C_1$–$C_6$)alkyl group;

$R_3$ a benzyl group with one or two substituents in the phenyl ring selected from hydrogen, halogen, cyano, amino, amino ($C_1$–$C_6$)alkyl, amino di ($C_1$–$C_6$)alkyl, amino ($C_1$–$C_6$)alkylacyl, aminophenacyl, amino (substituted) phenacyl, amino acid or derivative thereof, hydroxy, oxy ($C_1$–$C_6$)alkyl, oxyacyl, formyl, carboxylic acid, carboxamide, carboxy ($C_1$–$C_6$) alkylamide, carboxyphenylamide, carboxy ($C_1$–$C_6$) alkyl, hydroxy ($C_1$–$C_6$)alkyl, ($C_1$–$C_6$)alkyloxy ($C_1$–$C_6$) alkyl or acyloxy ($C_1$–$C_6$)alkyl, ($C_1$–$C_6$ alkylcarboxylic acid, or ($C_1$–$C_6$)alkylcarboxy ($C_1$–$C_6$)alkyl, amino ($C_1$–$C_6$)alkylacyl carboxylic acid or amino($C_1$–$C_6$) alkylcarboxylate; or a benzyl group with one substituent in the phenyl ring selected from groups of formula —$OCH_2CN$, —$OCH_2COR^8$ and —$OCH_2CH_2OR^9$, where $R^8$ is hydroxyl, ($C_1$–$C_6$)oxyalkyl, ($C_1$–$C_6$) oxyalkylphenyl, amino, ($C_1$–$C_6$)aminoalkyl, ($C_1$–$C_6$) aminodialkyl, ($C_1$–$C_6$)aminoalkylphenyl, an amino acid; and $R^9$ is ($C_1$–$C_6$)alkyl, ($C_1$–$C_6$)alkylphenyl, phenyl, phenyl ($C_1$–$C_6$)alkylacyl or phenacyl;

$R_4$ hydrogen or a ($C_1$–$C_6$)alkyl, or phenyl($C_1$–$C_6$)alkyl group;

$R_5$ hydrogen or methyl.

11. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

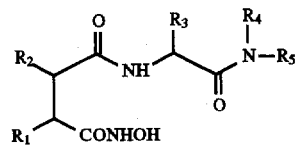

wherein the five substituents $R_1$–$R_5$ may vary as follows:

$R_1$ hydrogen, lower alkyl, aryl, or aryl lower alkyl;

$R_2$ hydrogen, lower alkyl, aryl, or aryl lower alkyl;

$R_3$ aryl lower alkyl, or heterocyclic lower alkyl, either being unsubstituted or mono- or di-substituted with fluoro, bromo, chloro, halo, nitro, carboxy, lower carbalkoxy, cyano, lower alkanoyl, trifluoromethyl lower alkyl, hydroxy, lower alkoxy, formyl, amino, lower alkyl amino, di-lower alkyl amino, mercapto, lower alkylthio, or mercapto lower alkyl;

$R_4$ a group —XD wherein X is a bond, lower alkylene, or a group —(CAB)$_m$—C(O)—N(Z)—, or —(CAB)$_m$—$CH_2O$—, or —(CAB)$_m$—C(O)O— wherein A is hydrogen, methyl or ethyl, and B and Z are independently hydrogen or lower alkyl, and m is 1, 2 or 3 with the proviso that when X is a chemical bond then the group $R_3$ is not unsubstituted benzyl or benzyl monosubstituted with hydroxy or lower alkoxy, and the further proviso that when X is a group —(CAB)$_m$—C(O)—N(Z)— wherein m is 1 and A, B and Z are as defined above, then the group $R_3$ is not indole or imidazole or unsubstituted benzyl or benzyl substituted with hydroxy or lower alkoxy, and wherein D is hydrogen or lower alkyl;

$R_5$ hydrogen or lower alkyl.

12. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

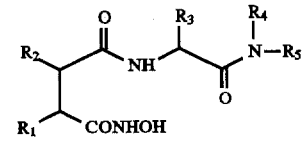

wherein the five substituents $R_1$–$R_5$ may vary as follows:

$R_1$ lower alkyl which may be substituted by a substituent selected from mercapto, loweralkylthio, arylthio and lower acylthio;

$R_2$ a group —Y—X—Z, wherein Y is a single bond or lower alkylene, X is O or S, and Z is lower alkyl;

$R_3$ 4-(lower alkyl)phenylmethyl;

$R_4$ lower alkyl;

$R_5$ hydrogen.

13. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

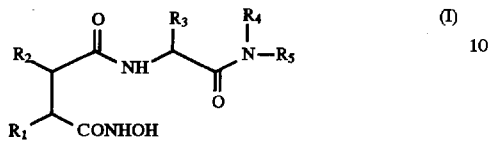

wherein the five substituents $R_1$–$R_5$ may vary as follows:

$R_1$ hydrogen;

$R_2$ hydrogen, alkyl, or aralkyl;

$R_3$ a group —$CH_2$—$CH_2$—$CH_2$—NH— where the right hand bond is formed with the N atom adjacent to the C atom carrying $R_3$, thereby replacing the H atom shown on that C atom in formula (I);

$R_4$ hydrogen, alkyl, alkoxy, or (when $R_5$ is hydrogen) —$CH(R^6)COR^7$ where $R^6$ is hydrogen or alkyl and $R^7$ is alkyl, or —$CH(R^6)COOR^8$ where $R^6$ is hydrogen or alkyl and $R^8$ is alkyl, or —$CH(R^6)CONR^9R^{10}$ where $R^9$ and $R^{10}$ are each alkyl, or $R^4$ taken together with $R^5$ and the nitrogen atom to which they are attached form a heterocyclic group;

$R_5$ hydrogen or alkyl.

14. A method for the inhibition of the release of and the effects of tumor necrosis factor (TNF) in a condition mediated by TNF in a mammal comprising administering to the mammal an effective amount of a matrix metalloproteinase (MMP) inhibitor derivative as defined by a compound of formula (I):

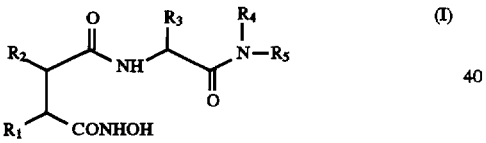

wherein the five substituents $R_1$–$R_5$ may vary as follows:

$R_1$ hydrogen, $C_1$–$C_6$ alkyl, $C_2$–$C_6$ alkenyl, phenyl, phenyl ($C_1$–$C_6$ alkyl), heterocyclyl, or a group $BSO_nA$- wherein n is 0, 1 or 2 and B is hydrogen or a ($C_1$–$C_6$) alkyl, phenyl, heterocyclyl, $C_1$–$C_6$ acyl, phenacyl, and A represents $C_1$–$C_6$ alkyl; amino; acylamino; OH; SH; $C_1$–$C_6$ alkoxy; $C_1$–$C_6$ alkylamino; $C_1$–$C_6$ alkylthio; aryl($C_1$–$C_6$ alkyl); amino($C_1$–$C_6$ alkyl); hydroxy ($C_1$–$C_6$ alkyl), mercapto($C_1$–$C_6$ alkyl) or carboxy ($C_1$–$C_6$ alkyl); lower alkyl substituted by maleimido, succinimido, naphthalimido, 2,3-dihydro-1,3-dioxo-1H-benz[d,e]isoquinol-2-yl, carbamoyl, mono(lower alkyl)carbamoyl, di(lower alkyl)carbamoyl, di(lower alkyl)amino, carboxy-lower alkanoylamino, pyrrolidino or morpholino;

$R_2$ ($C_1$–$C_6$)alkyl; ($C_2$–$C_6$)alkenyl; phenyl($C_1$–$C_6$)alkyl; cycloalkyl ($C_1$–$C_6$)alkyl; cycloalkenyl ($C_1$–$C_6$)alkyl; amino; carboxyl; esterified carboxyl; or a group —Y—X—Z wherein Y is a single bond or ($C_1$–$C_6$) alkylene, X is O or S, and Z is ($C_1$–$C_6$)alkyl;

$R_3$ $C_1$–$C_6$ alkyl; benzyl; benzyloxybenzyl; ($C_1$–$C_6$ alkoxy)benzyl; benzyloxy ($C_1$–$C_6$ alkyl); the characteristic side chain of a natural α amino acid; a group -[Alk]$_n$$R^6$ where Alk is an $C_1$–$C_6$ alkyl or $C_2$–$C_6$ alkenyl group optionally interrupted by one or more —O—, or —S— atoms or —N($R^7$)-groups (where $R^7$ is a hydrogen atom or a $C_1$–$C_6$ alkyl group), n is 0 or 1, and $R^6$ is a cycloalkyl or cycloalkenyl group; a benzyl group with one or two substituents in the phenyl ring selected from hydrogen, halogen, cyano amino, amino ($C_1$–$C_6$) alkyl, amino di ($C_1$–$C_6$)alkyl, amino ($C_1$–$C_6$)alkylacyl, aminophenacyl, amino(substituted)phenacyl, amino acid, hydroxy, oxy ($C_1$–$C_6$)alkyl, oxyacyl, formyl, carboxylic acid, carboxamide, carboxy ($C_1$–$C_6$) alkylamide, carboxyphenylamide, carboxy ($C_1$–$C_6$) alkyl, hydroxy ($C_1$–$C_6$)alkyl, ($C_1$–$C_6$)alkyloxy ($C_1$–$C_6$) alkyl or acyloxy ($C_1$–$C_6$)alkyl, ($C_1$–$C_6$)alkylcarboxylic acid, or ($C_1$–$C_6$)alkylcarboxy ($C_1$–$C_6$)alkyl, amino ($C_1$–$C_6$)alkylacyl carboxylic acid or amino($C_1$–$C_6$) alkylcarboxylate; or a benzyl group with one substituent in the phenyl ring selected from groups of formula —$OCH_2CN$, —$OCH_2COR^8$ and —$OCH_2CH_2OR^9$, where $R^8$ is hydroxyl, ($C_1$–$C_6$)oxyalkyl, ($C_1$–$C_6$) oxyalkylphenyl, amino, ($C_1$–$C_6$)aminoalkyl, ($C_1$–$C_6$) aminodialkyl, ($C_1$–$C_6$)aminoalkylphenyl, an amino acid; and $R^9$ is ($C_1$–$C_6$)alkyl, ($C_1$–$C_6$)alkylphenyl, phenyl, phenyl ($C_1$–$C_6$)alkylacyl or phenacyl; heterocyclic lower alkyl, either being unsubstituted or mono- or di-substituted with halo, nitro, carboxy, $C_1$–$C_6$ alkoxy, cyano, $C_1$–$C_6$ alkanoyl, trifluoromethyl $C_1$–$C_6$ alkyl, hydroxy, formyl, amino, $C_1$–$C_6$ alkyl amino, di-$C_1$–$C_6$ alkyl amino, mercapto, $C_1$–$C_6$ alkylthio, or mercapto $C_1$–$C_6$ alkyl; $C_1$–$C_6$ alkyl)phenylmethyl;

$R_4$ hydrogen, $C_1$–$C_6$ alkyl; a group —CHBD wherein B is H and D is H or $C_1$–$C_6$ alkyl, $C_1$–$C_6$ alkoxy-$C_1$–$C_6$ alkyl, di($C_1$–$C_6$ alkoxy)methyl, carboxy, $C_1$–$C_6$ alkylcarbonyl, $C_1$–$C_6$ alkoxycarbonyl, arylmethoxycarbonyl, $C_1$–$C_6$ alkylaminocarbonyl or arylaminocarbonyl; or $R_3$ and B together form a group ($CH_2$)n where n is an integer from 4–11; phenyl($C_1$–$C_2$ alkyl), or trifluoromethylphenyl($C_1$–$C_2$ alkyl); a group —($CH_2$)$_n$A wherein n is an integer from 1 to 6 and A represents the group —$NH_2$, a substituted acyclic amine, a heterocyclic base, hydroxy, ($C_1$–$C_6$)alkoxy , ($C_2$–$C_7$)acyloxy, ($C_1$–$C_6$)alkylthio, phenylthio, ($C_2$–$C_7$)acylamino or an N-pyrrolidone group; a straight or branched alkyl group, optionally interrupted by one or more —O— or —S— atoms or —N($R^7$)- groups (where $R^7$ is a hydrogen atom or a $C_1$–$C_6$ alkyl group), or aminocarbonyloxy groups; $C_1$–$C_6$ alkyl optionally substituted by aryl, amino, protected amino, di(lower alkyl)amino, guanidino, carboxyl, protected carboxyl, carbamoyl, mono(lower alkyl)carbamoyl, di(lower alkyl)carbamoyl, di(lower alkyl)phosphinyl, dihydroxyphosphinyl, pyrrolidino, piperidino or morpholino;

$R_5$ hydrogen.

15. A method for the inhibition of the release of and the effects of tumor necrosis factor (TNF) in a condition mediated by TNF in a mammal comprising administering to the mammal an effective amount of a matrix metalloproteinase (MMP) inhibitor derivative selected from the group consisting of:

2S-(4-methoxyphenylsulfanylmethyl)-3R-(2-phenyl-1S-methylcarbamoyl-ethylcarbamoyl)-5-methyl-hexanohydroxamic acid, 2S-(3-chlorophenylsulfanylmethyl)-3R-(2-phenyl-1S-methylcarbamoyl-ethylcarbamoyl)-5-methyl-hexanohydroxamic acid, 2S-(phenylsulfanylmethyl)-3R-(2-phenyl-1S-(pyrid-3-ylmethylcarbamoyl)-ethylcarbamoyl)-5-methyl-hexanohydroxamic acid, 2S-(3-methylphenylsulfanylmethyl)-3R-(2-phenyl-1S-methylcarbamoyl-ethylcarbamoyl)-5-methyl-hexanohydroxamic acid, 2S-(thien-2-ylsulphanylmethyl)-3R-(2-(4-carboxymethoxyphenyl)-1S-methylcarbamoyl-ethylcarbamoyl-5-methyl-hexanohydroxamic acid, 2S-thien-2-ylsulphanylmethyl)-3R-(2-phenyl-1S-(pyrid-3-ylmethylcarbamoyl)-ethylcarbamoyl)-5-methyl-hexanohydroxamic acid, 2S-(4-hydroxyphenylsulphanylmethyl)-3R-(2-phenyl-1S-(pyrid-3-ylmethylcarbamoyl)-ethylcarbamoyl)-5-methyl-hexanohydroxamic acid, 2S-(thien-2-ylsulfanylmethyl)-3R-(2-naph-2-yl-1S-methylcarbamoyl-ethylcarbamoyl)-5-methyl-hexanohydroxamic acid, 2S-(4-hydroxyphenylsulfanylmethyl)-3R-(2R-hydroxy-1S-methylcarbamoyl-propylcarbamoyl)-5-methyl-hexanohydroxamic acid, 2S-(4-hydroxyphenylsulfanylmethyl)-3R-(5-acetamido-1S-methylcarbamoyl-pentylcarbamoyl)-5-methyl-hexanohydroxamic acid, and 2S-(4-hydroxyphenylsulfanylmethyl)-3R-(3-[1,1-dimethylethoxycarbonyl]-1S-methylcarbamoyl-propylcarbamoyl 5-methyl-hexanohydroxamic acid.

16. A method for the inhibition of the release of and the effects of tumor necrosis factor (TNF) in a condition mediated by TNF in a mammal comprising administering to the mammal an effective amount of a matrix metalloproteinase (MMP) inhibitor derivative selected from the group consisting of:

2S-(thien-2-ylsufonylmethyl)-3R-(2-phenyl-1S-methylcarbamoyl-ethylcarbamoyl)-5-methyl-hexanohydroxamic acid, 3S-(2-[4-acetamido-phenyl]-1S-methylcarbamoyl-ethylcarbamoyl)-5-methyl-hexanohydroxamic acid, 2S-(4-phthalimido-butyl)-3R-(3-methyl-1S-ethoxycarbonylmethylcarbamoyl-butylcarbamoyl)-5-methyl-hexanohydroxamic acid, 3R-(2-[4-methoxy-phenyl]-1S-methylcarbamoyl-ethylcarbamoyl)-2S,5-dimethyl-hexanohydroxamic acid, 3R-(2-phenyl-1S-[2-oxo-pyrolid-1-yl]propylcarbamoyl-ethylcarbamoyl)-5-methyl-hexanohydroxamic acid, 3R-(2-[4-methoxy-phenyl]-1S-methylcarbamoyl-ethylcarbamoyl)-5-methyl-hexanohydroxamic acid, 3R-(2-phenyl-1S-[pyrid-3-ylmethylcarbamoyl]-ethylcarbamoyl)-5-methyl-hexanohydroxamic acid, 3R-(2,2-dimethyl-1S-methylcarbamoyl-propylcarbamoyl)5-methyl-hexanohydroxamic acid, and 2S-(thien-2-ylsulphanylmethyl)-3R-(2-(4-carboxymethoxyphenyl)-1S-methylcarbamoyl-ethylcarbamoyl)-5-methyl-hexanohydroxamic acid.

17. The method of any of claims 1 to 16, wherein said condition mediated by TNF is inflammation, fever, cardiovascular disorder, haemmorhage, coagulation, acute phase response, cachexia, anorexia, acute infection, shock state, graft versus host reaction or autoimmune disease.

18. The method of any of claims 1 to 16, wherein said condition mediated by TNF is septic shock, haemodynamic shock, sepsis syndrome, post ischaemic reperfusion injury, malaria, mycobacterial infection, meningitis, psoriasis, cancer, cachexia, fibrotic disease, congestive heart failure, graft rejection, rheumatoid arthritis, radiation damage, toxicity following administration of immunosuppressive monoclonal antibodies, hyperoxic alveolar injury, autoimmune disease, or any disease state in which TNF is a mediator of host injury.

* * * * *